United States Patent [19]

Davidson et al.

[11] 4,399,130

[45] Aug. 16, 1983

[54] USE OF METALLIC SALTS OF PYRIDINE-2-THIONE-N-OXIDE TO TREAT OR PREVENT SWINE EXUDATIVE EPIDERMITIS

[75] Inventors: Jeffrey Davidson, Tulare, Calif.; John G. Babish, Ithaca, N.Y.; John H. Wedig, Guilford, Conn.

[73] Assignee: Olin Corporation, New Haven, Conn.

[21] Appl. No.: 344,905

[22] Filed: Feb. 1, 1982

[51] Int. Cl.$^3$ .................. A61K 31/555; A61K 31/44
[52] U.S. Cl. .................................. 424/245; 424/263
[58] Field of Search .......................... 424/245, 263

[56] References Cited

U.S. PATENT DOCUMENTS 3,753,990  8/1973  Curry ................................... 424/49

OTHER PUBLICATIONS

Fukuzumi et al.-Chem. Abst., vol. 91, (1979), p. 70002e.
Blood et al., *Veterinary Medicine-Third Edition*, Bailliere, Tindall & Cassell, London (1971), pp. 894 and 895.
Wedig et al., *Toxicology and Applied Pharmacology*, vol. 36, pp. 255–259 (1976).
Adams et al., *Toxicology and Applied Pharmacology*, vol. 36, pp. 523–531 (1976).
Olin Corp. Literature Search #81-135.
Olin Corp. Product Brochure for Omadine ® brand sodium and zinc pyridine-2-thione-N-oxide products.
Chemical Abstracts 95, 215727q (1981).
Chemical Abstracts 95, 109372k (1981).
Chemical Abstracts 86, 606c (1977).
Cloyd et al., "Ocular Toxicity Studies with Zinc Pyridinethione", Toxicology and Applied Pharmacology, vol. 45, pp. 771–782 (1978).
Snyder et al., "Safety Evaluation of Zinc 2-Pyridinethiol 1-Oxide in a Shampoo Formulation", Toxicology and Applied Pharmacology, vol. 7, pp. 425–437 (1965).

*Primary Examiner*—Sam Rosen
*Attorney, Agent, or Firm*—William A. Simons; Thomas P. O'Day

[57] ABSTRACT

Described is a method for treating an animal for swine exudative epidermitis wherein said animal is administered an effective amount of at least one metallic salt of pyridine-2-thione-N-oxide.

5 Claims, No Drawings

USE OF METALLIC SALTS OF PYRIDINE-2-THIONE-N-OXIDE TO TREAT OR PREVENT SWINE EXUDATIVE EPIDERMITIS

BACKGROUND OF THE INVENTION

1. Field of the Invention

This invention relates to the use of metallic salts of pyridine-2-thione-N-oxide to prevent or treat swine exudative epidermitis.

2. Description of the Prior Art

Swine exudative epidermitis (also known as Greasy Pig Disease) is a skin disease of pigs ditinguished by the appearance of acute, generalized seborrhoeic dermatitis. The disease generally affects piglets under about 6 weeks of age, but occasionally groups of pigs up to about 3 months of age suffer from the disease. Many of the affected piglets die from the disease.

It is not certain exactly what bacteria causes the disease; but *Staphylococcus hyicus* is strongly suspected. The disease is particularly troublesome and of considerable economic importance because, once developed within a litter, often all piglets will be affected. Such affected piglets may have a diminished appetite. Progressive weakness in the piglets, followed by death in a few days, is the likely occurrence. See D. C. Blood and J. A. Henderson, *Veterinary Medicine* (Third Edition) Bailliere, Tindall & Cassell, London, pages 894 and 895.

Swine exudative epidermitis has in the past been treated by administering anti-infective agents such s antibiotics. However, it has been recently found to be very desirable to replace antibiotics by non-antibiotic drugs. For example, antibiotics effective in human medicine should not be utilized in veterinary medicine in order not to build up a strain resistance against bacteria appearing in human diseases. It is thus very important to find a method for the treatment of swine exudative epidermitis utilizing an active non-antibiotic chemical compound which substantially would overcome the drawbacks of antibiotics utilized so far.

Separately, the antimicrobial properties of metallic salts of pyridine-2-thione-N-oxide, known as [1-hydroxy-2(1H) pyridinethionato] salts, are well known. Such compounds have been employed in skin cleansing compositions and in antidandruff shampoo compositions. Another application of metallic salts of pyridine-2-thione-N-oxide is as a preservative against the growth of micro-organisms in compositions, for example, cosmetic compositions.

BRIEF SUMMARY OF THE INVENTION

The present invention, therefore, is directed to treating an animal for swine exudative epidermitis which comprises administering to said animal an effective amount of at least one metallic salt of pyridine-2-thione-N-oxide to treat or prevent swine exudative epidermitis.

DETAILED DESCRIPTION

As stated above, metallic salts of pyridine-2-thione-N-oxide are a well-known class of compounds and are generally made by reacting a metallic salt with 2-mercaptopyridine-N-oxide. Suitable metallic salts of pyridine-2-thione-N-oxide may be alkali metal salts such as sodium and heavy metal salts such as zinc, ferric ($Fe^{+3}$), cupric ($Cu^{+2}$), and other metal salts such as aluminum. Because of their commercial availability, the zinc and sodium salts of pyridine-2-thione-N-oxide are the most preferred metal salts.

The zinc salt of pyridine-2-thione-N-oxide, also known as bis[1-hydroxy-2(1H) pyridinethionato] zinc, is made by reacting a metallic salt (e.g., $ZnCl_2$ or $ZnSO_4$) with 2-mercaptopyridine-N-oxide. Exemplary methods for making this compound are disclosed in U.S. Pat. No. 2,809,971, which issued to Bernstein et al on Oct. 15, 1957, and in U.S. Pat. No. 4,080,329, which issued to Mantwyler on Mar. 21, 1978.

The sodium salt of pyridine-2-thione-N-oxide [also known as 2-pyridinethiol-1-oxide, Na salt] is generally made by reacting a 2-halopyridine-N-oxide (e.g., 2-chloropyridine-N-oxide) with sodium hydrosulfide (NaSH) in aqueous solution under a slightly alkaline condition or with a mixture of sodium sulfide ($Na_2S$) and sodium hydrosulfide. Exemplary methods for making this compound are disclosed in U.S. Pat. No. 2,686,786, which issued to Shaw et al on Aug. 17, 1954; U.S. Pat. No. 3,159,640, which issued to McClure et al on Dec. 1, 1964; and U.S. Pat. No. 3,892,760, which issued to Hooks et al on July 1, 1975.

Other metallic salts of pyridine-2-thione-N-oxide are disclosed in U.S. Pat. No. 3,347,863, which issued to ottman et al on Oct. 17, 1967, (aluminum); U.S. Pat. No. 3,953,450, which issued to Bouillon et al on Apr. 27, 1976, (aluminum); U.S. Pat. No. 2,809,971, which issued to Bernstein et al on Oct. 15, 1957, (manganese, nickel, ferric, ferrous, cupric, zinc, and many other heavy metal salts); and U.S. Pat. No. 4,209,506, which issued to Bouillon et al on June 24, 1980, (aluminum). All of these U.S. Patents are incorporated herein by reference in their entireties.

In practicing the process of the present invention, animals such as pigs under the age of about 3 months may be treated with an effective swine exudative epidermitis treating amount of at least one metallic salt of pyridine-2thione-N-oxide. It is to be understood that the term "an effective amount to treat or prevent swine exudative epidermitis" as used in the specification and claims herein is intended to include any amount or concentration that will treat or prevent swine epidermitis in such animals. Of course, this amount may be changed in response to numerous variables, such as the degree of effectiveness required, type of metal salt, whether animal is affected by the disease or not, and type of carrier, if any.

For most uses, an effective amount to treat or prevent swine exudative epidermitis would advantagously include administering from 1 to about 4 doses comprising from about 15 to about 200 milliliters of an aqueous suspension or dispersion containing about 1.5% to about 5.0% of zinc pyridine-2-thione-N-oxide (from about 255 mg to about 10,000 mg) or its weight equivalent of other metal salts in intervals from about 12 to about 48 hours. Preferably, said doses comprise from about 20 to about 50 milliliters of an aqueous suspension or dispersion containing about 2% to about 2.5% by weight zinc pyridine-2-thione-N-oxide per dose (from about 400 mg to about 1250 mg) and said doses are administered about each 12 to 24 hours. Furthermore, the active compound used in the present process may be combined with other known veterinary and pharmaceutical agents for further benefits.

This step of administering metallic salts of pyridine-2-thione-N-oxide such as the zinc salt to the animal is preferably accomplished in the form of a liquid suspension; i.e., the composition is sprayed onto the skin of the pig. Such compositions would comprise the active compound or compounds and at least one vehicle or carrier suitable for administration onto the skin of the animal.

Another preferred way of administering the active compound is by applying it in a cream or the like wherein the skin is covered with an effective amount of the active compound to treat or prevent swine exudative epidermitis.

Sometimes a piglet or mother pig (sow) should be treated, as a preventive measure, even if it is not clear whether the pig suffers from swine exudative epidermitis. For instance, in case it is clear that some animals of a piglet litter are suffering from swine exudative epidermitis, then one may want to treat all animals of said litter in order to assure that no further animals would be infected. Thus, prevention as well as treatment of this disease is contemplated within the scope of the invention.

If zinc pyridine-2-thione-N-oxide or another metallic salt or salts is combined with a solid or liquid vehicle or carrier before application, then any suitable methods for formulating and applying the active compound or compounds may be employed. Included in such suitable methods of application are emulsifiable liquids, suspensions, creams, and ointments.

Emulsifiable liquids may be prepared by dispersing the active compound or compounds in a vegetable oil or mineral oil, such as peanut oil, corn oil, soybean oil, sesame oil, and the like, and then admixing the thus formed suspensions with a suitable surfactant or emulsifier.

Suspensions are generally formed by dispersing the active compound or compounds in water or a suitable aqueous solution or other solvent.

Creams and ointments are generally made the same as emulsified liquids except at least one gelling agent or the like is additionally added. Such gelling agents may be natural axes like beeswax or aluminum fatty acid salts (e.g., stearates, palmitates, and oleates).

It should be clearly understood that any of the above-noted formulations, the ingredients which may make up such formulations other than the active compound or compounds and their dosage, and means for applying these formulations may include all known and conventional substances, amounts, and means, respectively, that are suitable for obtaining the desired swine exudative epidermitis treatment or prevention result. Therefore, such process parameters are not critical to the present invention.

Besides metallic salts of pyridine-2-thione-N-oxide, the present invention also contemplates the use of similar pyridine-2-thione-N-oxide compounds to treat swine exudative epidermitis. Specifically, the present invention contemplates the use of free 2-mercaptopyridine-N-oxide, organic salts (e.g., t-butylamine) and adducts of 2-mecaptopyridine-N-oxide, bis(pyridine-N-oxide) disulfide and its salt adducts (e.g., alkaline earth metal salts). The present invention also contemplates the use of similar compounds which have one or more other substituents on the pyridine ring (e.g., lower alkyl groups, $NO_2$, or halogens).

The following Examples further illustrate the present invention. All parts and percentages are by weight unless explicitly stated otherwise.

EXAMPLE 1

MINIMUM LETHAL CONCENTRATIONS (MLC) VALUES OF ZINC PYRIDINE-2-THIONE-N-OXIDE REQUIRED TO INHIBIT GROWTH OF STAPHYLOCOCCUS HYICUS

A freeze-dried culture of *Staphylococcus hyicus* was prepared for testing by inoculating it into a nutrient broth and incubating at 37° C. for 18 hours on a shaking waterbath. At testing, the culture had a density of 1 to $2 \times 10^9$ cells per milliliter.

A 1% by weight stock suspension of zinc pyridine-2-thione-N-oxide was made up and autoclaved at 121° C. for 20 minutes.

To 2.0 milliliters of top agar containing 0.75% by weight agar in Vogel-Bonner minimal media[1] were added 1 to $2 \times 10^3$ organisms and sufficient zinc pyridine-2-thione-N-oxide to yield concentrations of 0, 0.1, 1.0, 10, 100, and 1000 parts of that compound per million parts of solution. After vortexing, the contents of the tubes were prepared into nutrient agar plates and incubated for 18 hours at 37° C. Five plates were prepared at each dose level of zinc pyridine-2-thione-N-oxide.

The colonies of each plate were counted on an NBS Biotran II automatic colony counter. The average value of lethality observed of the 5 plates of each dose are given in Table 1 below.

TABLE 1

| Test Material | Percent Kill at Concentration of Test Material (ppm in top agar) | | | | | |
|---|---|---|---|---|---|---|
| | 0 | 1000 | 100 | 10 | 1 | 0.1 |
| zinc pyridine-2-thione-N—oxide | 0% | 100% | 100% | 100% | 99% | 86% |

[1]Vogel, H. J. and D. M. Bonner (1956) Acetylornithinase of *Escherichia coli*: partial purification and some properties. J. Biol. Chem., 218:97–106.

The MLC is generally defined as that concentration of test material lethal to 99% or more by weight of the organisms plated. As can be seen in Table 1, the MLC for zinc pyridine-2-thione-N-oxide was 1 ppm.

EXAMPLES 2 AND 3

MINIMUM LETHAL CONCENTRATIONS (MLC) VALUES OF SODIUM SALT OF PYRIDINE-2-THIONE-N-OXIDE AND THE MAGNESIUM SULFATE ADDUCT OF BIS(2-PYRIDYL-1-OXIDE) DISULFIDE REQUIRED TO INHIBIT GROWTH OF STAPHYLOCOCCUS HYICUS

The procedure of Example 1 was repeated except sodium pyridine-2-thione-N-oxide and the magnesium sulfate adduct of bis(2-pyridyl-1-oxide) disulfide $[(C_5H_4NOS)_2 \cdot MgSO_4 \cdot 3H_2O]$ were employed as active compounds instead of the zinc salt. Again, the colonies of each plate were counted on an NBS Biotran II automatic colony counter. The average value of lethality observed of the 5 plates of each dose are given in Table 1A below.

TABLE 1A

| Test Material | Percent Kill at Concentration of Test Material (ppm in top agar) | | | | | |
|---|---|---|---|---|---|---|
| | 0 | 1000 | 100 | 10 | 1 | 0.1 |
| sodium pyridine-2-thione-N—oxide | 0 | 100% | 100% | 100% | 96% | 0 |
| magnesium sulfate adduct of bis (2-pyridyl-1-oxide) disulfide | 0 | 100% | 100% | 100% | 96% | 0 |

As can be seen, the MLC for both of these test materials was 10 ppm.

EXAMPLE 4

A clinical study was carried out to assess the effectiveness of zinc pyridine-2-thione-N-oxide in the treatment of swine exudative epidermitis. 53 young pigs with clinical signs of exudative epidermitis were sprayed with about 20 to about 30 ml of an aqueous suspension containing 2% by weight zinc pyridine-2-thione-N-oxide daily for up to 4 days. Separately, a control group of 26 young pigs with similar clinical signs were sprayed with the same aqueous vehicle daily, except no zinc pyridine-2-thione-N-oxide was in this vehicle.

The severity of the disease was scored for each pig for 4 days using the following 1 to 5 scoring system:

1. Normal
2. Very mild exudative epidermitis (EE) (about 15% of body surface affected)
3. Moderate EE (about 15% to about 20% of body surface affected)
4. Moderate EE to Severe EE (about 25% to about 50% of the body affected)
5. Very severe EE (more than about 50% of body affected)

Death was given no point value in this system.

The results of the scoring of this study are given in Tables 2 and 3.

To assess the rate at which the animals were returning to normal appearance, the percent of animals achieving a score of 1 was calculated. As can be seen, after 1 day approximately 4% of the treated animals appeared normal. This percentage increased to 25% by day 4. During the same period, approximately 9% of the controls were scored normal; this figure compares well with the spontaneous recovery rate estimated in this area.

Since the number of animals scored normal after 4 days is highly dependent upon initial scores of severity, perhaps a better indicator of effectiveness of treatment is clinical improvement. For the purposes of this study, clinical improvement was defined as a reduction of the day 1 score by 2 or more units by day 4. Approximately 54% of the test animals exhibited clinical improvement as compared with only 9% of the controls.

Therefore, it could be reasonably concluded that the repeated dermal application of 2% suspension of zinc pyridine-2-thione-N-oxide to pigs with clinical signs of swine exudative epidermitis resulted in significant improvement of the clinical signs compared to similarly treated vehicle control animals.

TABLE 2

INDIVIDUAL SCORES[a] OF YOUNG PIGS RECEIVING 2% ZINC PYRIDINE-2-THIONE-N—OXIDE DERMALLY OVER THE FOUR-DAY OBSERVATION PERIOD

| Pig No. | Day | | | |
|---|---|---|---|---|
| | 1 | 2 | 3 | 4 |
| 1 | 3 | 3 | 2 | 1 |
| 2 | 3 | 3 | 3 | 2 |
| 3 | 3 | 2 | 2 | 2 |
| 4 | 2 | 2 | 1 | 1 |
| 5 | 2 | 2 | 1 | 1 |
| 6 | 3 | 3 | 3 | 1 |
| 7 | 3 | 3 | 2 | 2 |
| 8 | 5 | 5 | 4 | 3 |
| 9 | 5 | Dead | | |
| 10 | 3 | 3 | 2 | 2 |
| 11 | 4 | 4 | 3 | 3 |
| 12 | 4 | 4 | 3 | 3 |
| 13 | 3 | 3 | 2 | 2 |
| 14 | 3 | 2 | 2 | 1 |
| 15 | 3 | 2 | 2 | 2 |
| 16 | 4 | 4 | 3 | 1 |
| 17 | 3 | 2 | 2 | 2 |
| 18 | 4 | 2 | 2 | 2 |
| 19 | 5 | 5 | 4 | 4 |
| 20 | 4 | 4 | 3 | 2 |
| 21 | 3 | 3 | 2 | 2 |
| 22 | 3 | 2 | 2 | 2 |
| 23 | 2 | 2 | 1 | 1 |
| 24 | 4 | 4 | 3 | 3 |
| 25 | 4 | 3 | 3 | 3 |
| 26 | 3 | 3 | 2 | 3 |
| 27 | 5 | 5 | 4 | 3 |
| 28 | 5 | 5 | 4 | 2 |
| 29 | 2 | 1 | 1 | 2 |
| 30 | 3 | 3 | 2 | 2 |
| 31 | 3 | 2 | 1 | 1 |
| 32 | 5 | 3 | 3 | 2 |
| 33 | 4 | 2 | 2 | 2 |
| 34 | 5 | 4 | 2 | 1 |
| 35 | 5 | 4 | 3 | 1 |
| 36 | 3 | 1 | 2 | 1 |
| 37 | 5 | 5 | 2 | 1 |
| 38 | 4 | 3 | 3 | 3 |
| 39 | 5 | 5 | 2 | 2 |
| 40 | 4 | 3 | 3 | 2 |
| 41 | 3 | 2 | 2 | 2 |
| 42 | 4 | 4 | 2 | 2 |
| 43 | 4 | 4 | 3 | 3 |
| 44 | 3 | 2 | 2 | 2 |
| 45 | 5 | 4 | 5 | 3 |
| 46 | 4 | 3 | 3 | 2 |
| 47 | 4 | 3 | 3 | 2 |
| 48 | 4 | 4 | 2 | 2 |
| 49 | 3 | 2 | 2 | 2 |
| 50 | 4 | 3 | 2 | 2 |
| 51 | 5 | 4 | 4 | 5 |
| 52 | 5 | 5 | 4 | 4 |
| 53 | 2 | 2 | 1 | 1 |

[a]1 = normal; 2 = very mild EE; 3 = moderate EE; 4 = moderate to severe EE; 5 = very severe EE

TABLE 3

INDIVIDUAL SCORES[a] OF CONTROL YOUNG PIGS RECEIVING ONLY VEHICLE DERMALLY OVER THE FOUR-DAY OBSERVATION PERIOD

| Pig No. | Day | | | |
|---|---|---|---|---|
| | 1 | 2 | 3 | 4 |
| C1 | 2 | 2 | 2 | 2 |
| C2 | 2 | 2 | 2 | 2 |
| C3 | 5 | Dead | | |
| C4 | 2 | 2 | 2 | 2 |
| C5 | 3 | 3 | 3 | 4 |
| C6 | 2 | 2 | 3 | 3 |
| C7 | 2 | 2 | 3 | 3 |
| C8 | 3 | 3 | 2 | 3 |
| C9 | 2 | 2 | 2 | 1 |
| C10 | 3 | 3 | 4 | 5 |

TABLE 3-continued

INDIVIDUAL SCORES[a] OF CONTROL YOUNG PIGS RECEIVING ONLY VEHICLE DERMALLY OVER THE FOUR-DAY OBSERVATION PERIOD

| Pig No. | Day | | | |
|---|---|---|---|---|
| | 1 | 2 | 3 | 4 |
| C11 | 3 | 3 | 2 | 2 |
| C12 | 3 | 3 | 5 | 4 |
| C13 | 3 | 2 | 2 | 3 |
| C14 | 2 | 2 | 2 | 2 |
| C15 | 4 | 4 | 4 | Dead |
| C16 | 3 | 3 | 2 | 2 |
| C17 | 3 | 3 | 4 | 3 |
| C18 | 3 | 3 | 3 | 3 |
| C19 | 3 | 3 | 4 | 4 |
| C20 | 4 | 4 | 3 | 3 |
| C21 | 3 | 3 | 4 | 4 |
| C22 | 4 | 4 | 3 | 4 |
| C23 | 3 | 2 | 2 | 1 |
| C24 | 5 | 5 | 5 | Dead |
| C25 | 3 | 3 | 3 | 3 |
| C26 | 3 | 3 | 2 | 3 |

[a] 1 = normal; 2 = very mild EE; 3 = moderate EE; 4 = moderate to severe EE; 5 = very severe EE

What is claimed is:

1. A method of treating an animal for swine exudative epidermitis which comprises administering to said animal an effective amount of at least one metallic salt of pyridine-2-thione-N-oxide to treat or prevent swine exudative epidermitis.

2. The method of claim 1 wherein said administration is applied to the skin of a pig.

3. The method of claim 2 wherein from 1 to about 4 doses of an aqueous suspension containing about 15 to about 200 milliliters of water containing from 1.5% to 5.0% by weight of zinc pyridine-2-thione-N-oxide are administered to the skin of said pig at intervals of 12 to 48 hours.

4. The method of claim 2 wherein said pig is treated when it has the clinical symptoms of the disease.

5. The method of claim 2 wherein said pig is under about 3 months in age.